United States Patent [19]

Graser

[11] Patent Number: 5,891,161
[45] Date of Patent: Apr. 6, 1999

[54] WIRE INSERTION GUIDE AND METHOD OF USE IN PINNING BONES

[76] Inventor: Robert E. Graser, 7333 Barlite, Suite 330, San Antonio, Tex. 78224

[21] Appl. No.: 977,102

[22] Filed: Nov. 24, 1997

[51] Int. Cl.[6] .................................................. A61B 17/04
[52] U.S. Cl. ................................ 606/148; 606/59; 81/342
[58] Field of Search ..................................... 606/148, 144, 606/139, 145, 147, 87, 59, 157, 179; 81/342, 318–323

[56] References Cited

U.S. PATENT DOCUMENTS

| | | | |
|---|---|---|---|
| 5,207,712 | 5/1993 | Cohen | 606/59 X |
| 5,746,757 | 5/1998 | McGuire | 606/148 |

*Primary Examiner*—Michael Buiz
*Assistant Examiner*—Vikki Trinh
*Attorney, Agent, or Firm*—Jenkens & Gilchrist

[57] ABSTRACT

Two semicylindrical bodies, each mounted on a respective end of one member of a pair of pivotally interconnected blades, are closed to form a cylindrical body having a first end in which a frustoconical surface is arranged to guide a wire into a central bore, and a second end communicating with bore and in which a semi-spherical cavity is shaped to receive a bone end. The wire insertion guide is particularly applicable to procedures such as resectional arthroplasties requiring K-wire fixation, Hoffman-Clayton type rheumatoid forefoot reconstructive procedures, and procedures relating to finger reconstruction.

15 Claims, 3 Drawing Sheets

WIRE INSERTION GUIDE AND METHOD OF USE IN PINNING BONES

BACKGROUND OF THE INVENTION

1. Technical Field

This invention relates generally to a device for positioning a wire on a bone end preparatory to inserting the wire into the bone and to a method of using the wire insertion guide device for pinning at least two elongated bones, or bone portions together, and more particularly to such a wire insertion guide that has a first end adapted to guide the wire through a central bore of the device and a second end shaped to receive a bone end, and to a method wherein the wire is inserted through the bone end and through a central canal of an elongated bone, such as a bone of a toe or finger.

2. History of Related Art

Many surgical procedures such as resectional arthroplasties and Hoffman-Clayton type rheumatoid forefoot reconstructive procedures where the metatarsal head is resected along with the resectional arthroplasty of the proximal phalanx, generally require that the proximal phalangeal and metatarsal bones are held in straight alignment with the aid of a Kirshner's wire (K-wire). Heretofore, the K-wire has been inserted through the distal end of the phalanges and moved through the phalanges to the metatarsal, and then through the central canal of the metatarsal. A common problem with the procedure is guidance of the K-wire into the end of the metatarsal so that the wire is aligned to follow the central aspect of the metatarsal bone. In order to carry out the procedure, it was necessary to maintain the phalanges in precise alignment with the metatarsal while inserting the K-wire. Because of the small diameter of the K-wire and the limited space between the bones, it was often difficult to determine whether or not the advancing end of the K-wire was aligned, both laterally and vertically, with the central canal of the metatarsal.

Similar problems with guiding a wire during insertion into elongated digital bones are found in procedures involving of bones in a finger.

The present invention is directed to overcoming the problem set forth above. It is desirable to have a simple, manually operable device that guides a wire from the end of a first bone toward the end of a second bone, while simultaneously aligning the wire so that it is directed in a desired orientation with respect to the second bone. It is also desirable to have a method for pinning two bones together, using the wire insertion guide embodying the present invention, so that the wire is accurately positioned and guided during insertion of the wire through the second bone.

SUMMARY OF THE INVENTION

In accordance with one aspect of the present invention, a wire insertion guide for positioning a wire on a bone end preparatory to inserting the wire into the bone has a pair of blades that are pivotally interconnected at an intermediate position along their lengths for relative movement through respective parallel planes between a closed position, at which respective first ends of each of the blades are disposed in abutting relationship, and an open position at which the respective first ends are disposed in spaced apart relationship from each other. A semicylindrical body is attached to the first end of each of the blades. When the blades are moved to the closed position the semicylindrical bodies are moved into abutting relationship with each other where they co-operate to form a closed cylindrical structure having a frustoconical surface at a first end, a cup-shaped cavity at the second end, and a central bore extending through the closed cylindrical structure between the frustoconical surface and the cup-shaped cavity.

Other features of the wire insertion guide include the guide having a means for maintaining the blades at the closed position. Additional features include a second end of each of the blades being shaped to receive a finger of a person operating the wire insertion guide, the frustoconical surface at the first end of the closed semicylindrical bodies having an included angle of about 100°, and the cup-shaped cavity at the closed second ends of the semicylindrical bodies being shaped to receive the end of a bone from which a portion has been removed.

In accordance with another aspect of the present invention, a method for pinning at least two elongated bones or bone portions together includes inserting a K-wire through a first end of a first bone and drawing the K-wire, by moving the K-wire in a first direction, through the first bone so that a portion of the K-wire extends from a second end of the first bone. A wire insertion guide is inserted between the first end of the first bone and the first end of a second bone, and the K-wire is moved in a second direction opposite to that of the first direction and threaded through the wire insertion guide. The K-wire then is inserted through the first end of the second bone and moved through the second bone until the wire is at a selected position in the second bone.

Other features of the method of pinning at least two elongated bones or bone portions together, embodying the present invention, include the first bone being a middle phalangeal bone, the second bone being a metatarsal bone, and the method includes, prior to positioning a wire insertion guide against the first end of a second bone, resecting the distal end of the metatarsal bone. Additional features of the method include resectional arthroplasty of the proximal phalangeal bone prior to inserting a K-wire through the first end of the first bone. Additional features of the method embodying the present invention include moving the K-wire in the first direction, after inserting the K-wire through the first end of the first bone, whereby the K-wire is moved through the middle phalangeal bone and a distal phalangeal bone so that a portion of the K-wire extends from a distal end of the distal phalangeal bone.

Yet additional features of the method include, subsequent to inserting the K-wire through the middle and distal phalangeal bones, moving the K-wire in a second direction opposite to the first direction and inserting the K-wire through a proximal phalangeal bone prior to threading the K-wire through the wire insertion guide. Yet another feature of the method for pinning at least two elongated bones or bone portions together, embodying the present invention, includes subsequent to inserting the K-wire through the first end of the second bone, moving the K-wire through the longitudinal central canal of the metatarsal bone until it reaches the most proximal cortical end of the metatarsal bone whereat it is firmly fixated within cortical bone.

BRIEF DESCRIPTION OF THE DRAWINGS

A more complete understanding of the structure and operation of the present invention may be had by reference to the following detailed description when taken in conjunction with the accompanying drawings, wherein.

DETAILED DESCRIPTION OF PRESENTLY PREFERRED EXEMPLARY EMBODIMENTS

Figure 1:
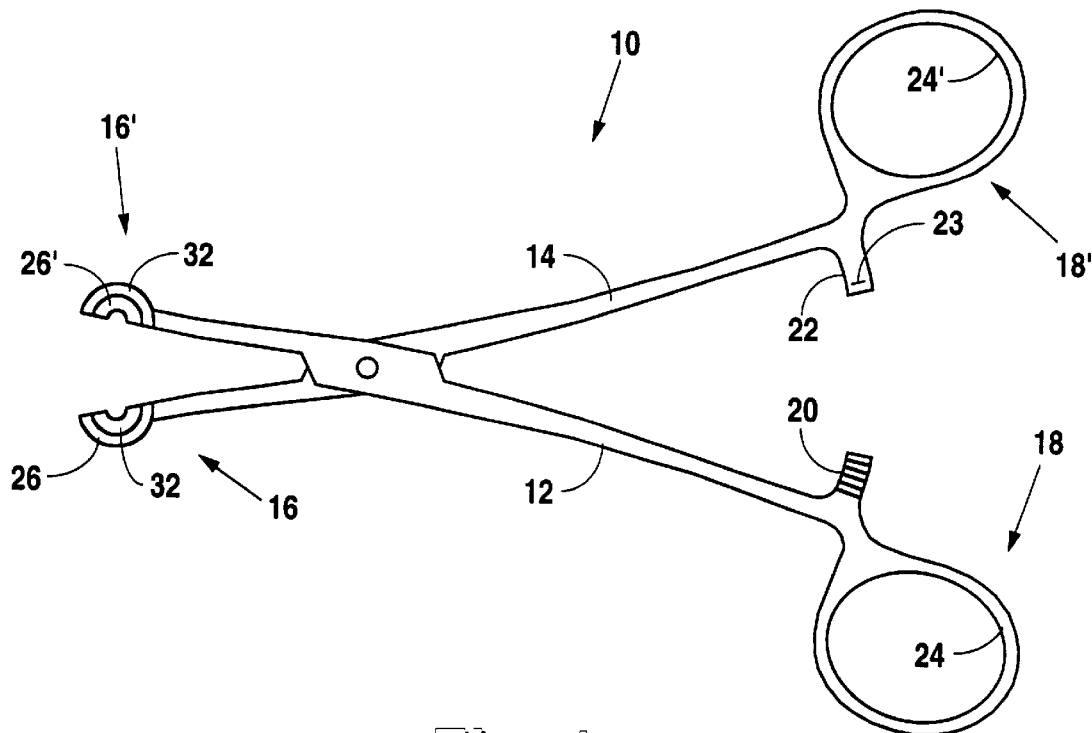
FIG. 1 is a top plan view of the wire insertion guide embodying the present invention, showing the guide in an open position.
Figure 2:
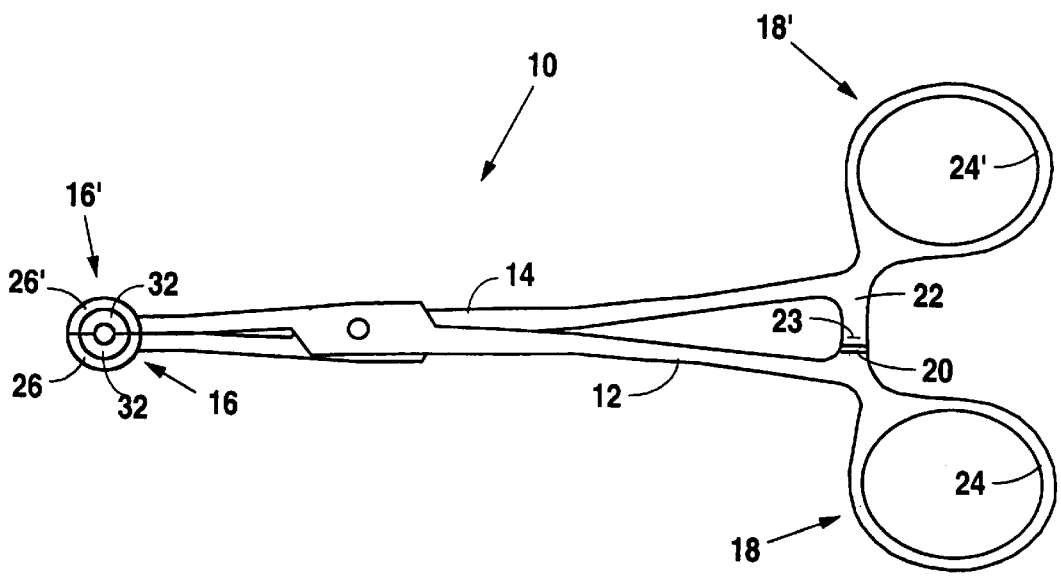
FIG. 2 is a top plan view of the wire insertion guide embodying the present invention, showing the guide in a closed position.
Figure 3:
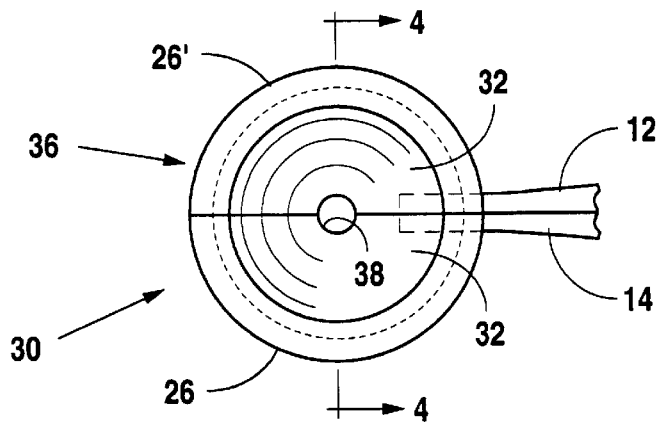
FIG. 3 is an enlarged top plan view of the wire guide end of the wire insertion device embodying the present invention, showing the wire guide end in a closed position.

In the preferred embodiment of the present invention, a wire insertion guide includes a first blade 12 pivotally interconnected with a second blade 14, each of which have a respective first end 16, 16' and a respective second end 18, 18'. The first and second blades 12, 14, are pivotally interconnected at a position intermediate the first and second ends 16, 16', 18, 18' and are moveable in respective parallel planes between an open position, as shown in FIG. 1 and a closed position as illustrated in FIG. 2. The blade portion of the wire insertion guide 10 has a construction similar to, or may actually be, a conventional hemostat which advantageously has a means for maintaining the first ends 16, 16' of the blades 12, 14 in clamped relationship at the closed position. As illustrated in FIGS. 1 and 2, the means for maintaining the first ends 16, 16' in the closed position includes a ribbed arm 20 extending outwardly from the first blade 12 towards the second blade 14. An arm 22, has a tooth 23, projecting downwardly as viewed in FIGS. 1 and 2 from the second blade 14, that is biased toward and adapted to engage a selected groove between the ribs on the ribbed arm 20 when the first and second blades are moved to the closed position shown in FIG. 2. The operation of the hemostat clamp mechanism is well-known, and is closed by inserting a thumb and finger through respective loops 24, 24' provided on the second ends 18, 18' of the blades 12, 14, and moving the second ends 18, 18' toward each other until the tooth 23 is tightly seated in a groove of the ribbed arm 20.

A generally semicylindrical body 26, 26' is attached to the respective first end 16, 16' of the blades 12, 14 by silver solder or welding. Both the hemostat portion and the semicylindrical body portions 26, 26' are preferably formed of stainless steel.

Figure 4:
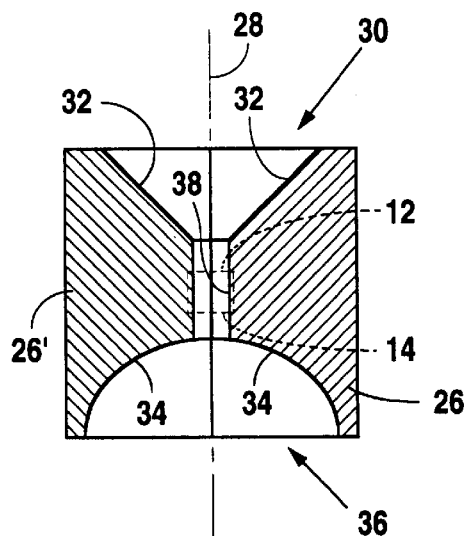
FIG. 4 is a sectional view of the guide end of the wire insertion device embodying the present invention, taken along the line 4—4 of FIG. 3.
Figure 5:
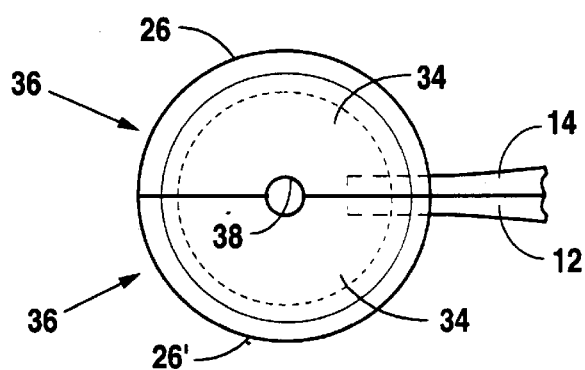
FIG. 5 is a bottom plan view of the wire guide end of the wire insertion device embodying the present invention, showing the wire guide end in a closed position.

As best shown in FIG. 4, each of the semicylindrical bodies 26, 26' have, when at the closed position, a common longitudinal axis 28 that is perpendicular to the parallel planes through which the blades 12, 14 are translated when moved between the open and closed positions. When the semicylindrical bodies 26, 26' are at the closed position, they cooperate to define a first end 30 having a frustoconically shaped surface 32 converging radially inwardly from the first end 30, and a spherically shaped cavity 34, extending inwardly from a second end 36 of the abutting semicylindrical bodies 26, 26'. Each of the semicylindrical bodies 26, 26' have a semicylindrical bore extending along the longitudinal axis 28 which cooperate to provide a cylindrical bore 38 extending through the closed cylindrical bodies 26, 26' between the frustoconically-shaped surface 32 and the spherically-shaped cavity 34.

The frustoconically-shaped surface 32 provides a funnel-shaped wire guide at the first end 30 of the closed semicylindrical bodies 26, 26', and the spherically-shaped cavity 34 provides a cup-shaped cavity that is adapted to receive the end of a bone from which a portion has been removed, as described below in more detail. The cylindrical bore 38 extending between the frustoconically-shaped surface 32 and the spherically-shaped cavity 34 of the closed semicylindrical bodies 26, 26' has a diameter only slightly greater than the predefined diameter of a wire that is inserted through the wire insertion guide 10. For example, in the preferred embodiment of the present invention, the cylindrical base has a diameter of about 0.047 in (1.19 mm), a diameter found to be desirable for guiding a K-wire having a diameter of about 0.045 in (1.14 mm). Preferably, the frustoconically-shaped surface 32 at the first end 30 of the closed semicylindrical bodies 26, 26' has an included angle of about 100°.

Figure 6A:
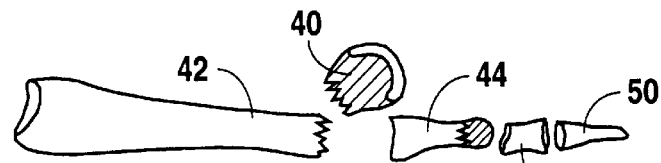
FIGS. 6A–6G collectively illustrate the steps carried out in one embodiment of the method for pinning at least two bones or bone portions together, in accordance with the present invention.
Figure 6B:
Figure 6C:
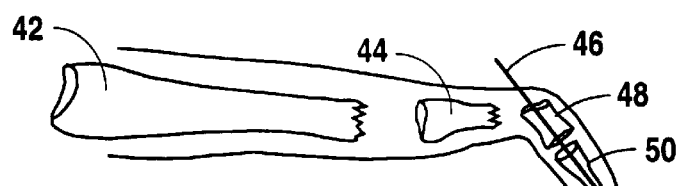
Figure 6D:
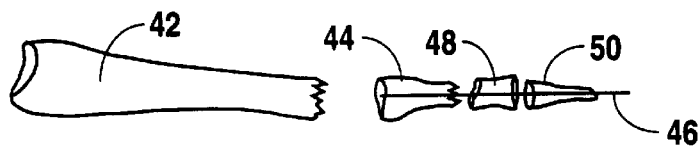

Turning now to FIGS. 6A–6G, the use of the wire insertion guide 10 is described in association with a method of pinning at least two elongated bones or bone portions. The wire insertion guide 10 is particularly useful in procedures such as resectional arthroplasties requiring Kirshner's wire (K-wire) fixation, as well as Hoffman-Clayton type rheumatoid forefoot reconstruction procedures where the metatarsal head is resected along with resectional arthroplasty of a proximal phalanx, and the two held in straight alignment with a K-wire. In these procedures, a metatarsal head 40 is resected from a metatarsal bone 42, as shown in FIG. 6A, and then the proximal phalangeal bone is resected as shown in FIG. 6B. A K-wire 46 is inserted through the middle phalanx 48 and a co-digitally disposed distal phalanx and pulled out at the end of the two so that a portion of the K-wire 46 extends beyond the toe as shown in FIG. 6C. The K-wire 46 is then retrograded into the proximal phalangeal bone 44 as shown in FIG. 6D.

Figure 6E:
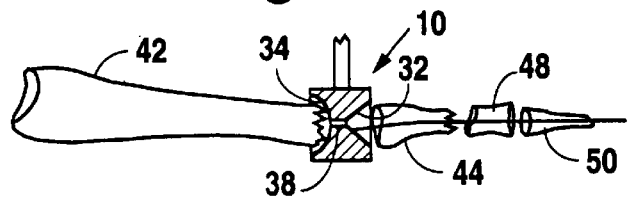

The wire insertion guide 10 is clamped closed, one click, at the closure mechanism 20, 22. The wire insertion guide 10 is then inserted between the metatarsal bone 42 and the proximal phalanx 44, as shown in FIG. 6E, with the frustoconically-shaped first end 30 positioned against the base of the proximal phalanx 44 and the cup-shaped cavity at the second end 36 in contact with the stump of the transacted metacarpal bone neck. The longitudinal axis 28 of the wire insertion guide 10 is aligned with the longitudinal central canal of the metatarsal bone 42. Advantageously, the cylindrical bore 38 is co-axially aligned with the longitudinal axis 28 of the wire insertion guide 10, so that when the blades 12, 14 are positioned perpendicular to the longitudinal central canal of the metatarsal bone 42, the cylindrical bore 38 is likewise aligned with the central aspect of the metatarsal bone 42.

Following positioning of the wire insertion guide 10, the wire is retrograded from the distal end of the digit, be it a finger or toe, toward the wire insertion guide 10. As the K-wire 46 hits the frustoconically-shaped first end 30 of the wire insertion guide 10, the wire 46 contacts the frustoconically-shaped surface 32, and slides along the conical surface 32 to the closely toleranced central bore 38. The central bore 38 aligns the K-wire 46 within the wire insertion guide 10 and, as the wire insertion guide 10 is also placed against the stump of the transected metatarsal bone neck, the cylindrical bore 38 is aligned with the longitudinal central canal of the metatarsal bone 42.

Figure 6F:
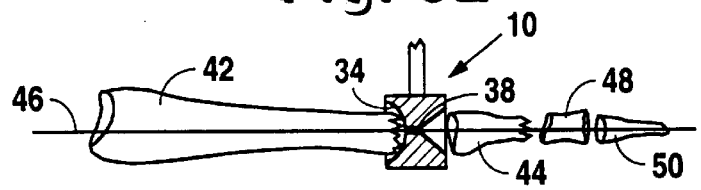
Figure 6G:
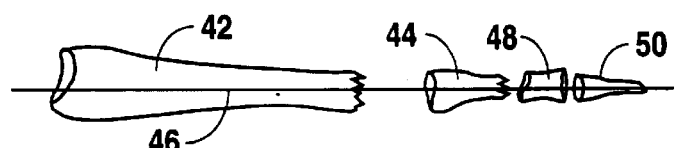

The K-wire 46 is then forwarded, by power instrumentation, through the wire insertion guide 10 and up through the central aspect of the metatarsal bone 42 until it reaches the most proximal cortical end of the metatarsal bone 42 whereat it is firmly fixated within cortical bone, as shown in FIG. 6F. The blades 12, 14 of the wire insertion guide 10 are then opened, whereupon the semicylindrical bodies 26, 26' are moved away from each other to allow easy removal of the wire insertion guide 10 from the small wound area, and the procedure concluded.

Thus, it can be seen that the wire insertion guide 10 embodying the present invention provides a simple, yet accurate method of aligning a wire used to join two bones. The wire insertion guide overcomes the present problem of accurately aligning the wire with a central canal of an elongated bone into which the wire is to be inserted.

Although the present invention is described in terms of a preferred exemplary embodiment in which the method the embodying the present invention was described with specific reference to the bones of a toe, those skilled in the art will recognize that the wire insertion guide, and method of using the guide, is also applicable to procedures in which the bones of a finger are pinned. Such uses are intended to fall within the scope of the following claims. Other aspects, features and advantages of the present invention may be obtained from a study of this disclosure and the drawings, along with the appended claims.

What I claim is:

1. A wire insertion guide for positioning a wire on a bone end preparatory to inserting the wire into the bone, comprising:

a pair of blades each having a first end and a second end and being pivotally interconnected at an position intermediate said first and second ends and movable through respective parallel planes between a closed position at which said respective first ends are disposed in abutting relationship and an open position at which said respective first ends are disposed in spaced apart relationship from each other;

a semicylindrical body attached to the first end of each blade, each of said semicylindrical bodies having an axis perpendicular to a respective one of said parallel planes, a first end, and a second end longitudinally spaced apart along said axis from said first end of the body, said first end of the body, having a conically-shaped surface converging radially inwardly from said first end of the body, said second end of the body, having a generally spherically-shaped cavity extending inwardly from said second end of the body, and said body having a semicylindrical bore extending along said axis between said conically-shaped surface and said spherically-shaped cavity, said semicylindrical bodies being moved into abutting relationship with each other whereat said respective axes are coaxially aligned and said semicylindrical bodies cooperate to form a closed cylindrical structure when said blades are at said closed position, said closed cylindrical structure providing a frustoconical wire guide at the abutting first ends of the semicylindrical bodies, a cup-shaped cavity at the abutting second ends of the semicylindrical bodies, and a central bore extending through said closed cylindrical structure between said frustoconical wire guide and said cup-shaped cavity.

2. A wire insertion guide, as set forth in claim 1, wherein each of said guide includes a means for maintaining said blades at said closed position.

3. A wire insertion guide, as set forth in claim 1, wherein the second end of each of said blades is shaped to receive a finger or thumb of a person operating said wire insertion guide.

4. A wire insertion guide, as set forth in claim 1, wherein the frustoconical wire guide at the abutting first ends of the semicylindrical bodies has an included angle of about 100 degrees.

5. A wire insertion guide, as set forth in claim 1, wherein the cup-shaped cavity at the abutting second ends of the semicylindrical bodies is shaped to receive the end of a bone from which a portion has been removed.

6. A method of pinning at least two elongated bones or bone portions together, comprising:

inserting a K-wire through a first end of a first bone and drawing said K-wire, by moving said K-wire in a first direction, through said first bone so that a portion of said K-wire extends from a second end of said first bone;

positioning a wire insertion guide against the first end of a second bone;

moving said K-wire in a second direction opposite to said first direction;

threading said K-wire through said wire insertion guide;

inserting said K-wire through the first end of said second bone;

moving said K-wire through said second bone until said wire is at a selected position in said second bone, wherein said wire insertion guide includes a pair of semicylindrical bodies, each of said semicylindrical bodies being respectively mounted on one of a pair of pivotally interconnected blades disposed in parallel planes perpendicular to a centrally disposed bore of said wire insertion guide, each of said semicylindrical bodies having an axis perpendicular to a respective one of said parallel planes, a first end and a second end of said body being longitudinally spaced apart along said axis from said first end of said body; and wherein said first end of said body having a conically-shaped surface converging radially inwardly from said first end of said body, said second end of said body having a generally spherically-shaped cavity extending inwardly from said second end of said body, and said bore extending along said axis between said conically-shaped surface and said spherically-shaped cavity, said semicylindrical bodies being moved into abutting relationship with each other whereat said respective axes are coaxially aligned and said semicylindrical bodies cooperate to form a closed cylindrical structure when said blades are at closed position, said closed cylindrical structure providing a frustoconical wire guide at the abutting first ends of the semicylindrical bodies, a cup-shaped cavity at the abutting second ends of the semicylindrical bodies, and said central bore extending through said closed cylindrical structure between said frustoconical wire guide and said cup-shaped cavity.

7. A method of pinning at least two elongated bones or bone portions together, as set forth in claim 6, wherein said first bone comprises a proximal phalangeal bone and said second bone comprises a co-digitally disposed metatarsal bone and said method includes, prior to positioning a wire insertion guide against the first end of a second bone, resecting the distal end of the metatarsal bone.

8. A method for pinning at least two elongated bones or bone portions together, as set forth in claim 7, wherein said method includes, prior to inserting a K-wire through the first end of the first bone, resectional arthroplasty of the proximal phalangeal bone.

9. A method for pinning at least two elongated bones or bone portions together, as set forth in claim 7, wherein said first bone comprises a middle phalangeal bone and said inserting a K-wire through the first end of the first bone includes inserting the K-wire, by moving the K-wire in said first direction through the middle phalangeal bone and a codigitally disposed distal phalangeal bone with said proximal phalangeal bone so that a portion of the K-wire extends beyond a distal end of said distal phalangeal bone.

10. A method for pinning at least two elongated bones or bone portions together, as set forth in claim 9, wherein subsequent to inserting the K-wire through the middle and distal phalangeal bones, said method includes moving said wire in said second direction and inserting said K-wire through a proximal phalangeal bone codigitally disposed with said middle and said distal phalangeal bones, prior to said threading said K-wire through said wire insertion guide.

11. A method for pinning at least two elongated bones or bone portions together, as set forth in claim 10, wherein said positioning a wire insertion guide against the first end of a second bone includes positioning said wire insertion guide between a distal end of said metatarsal bone and the proximal end of said proximal phalangeal bone, and aligning said central bore of said wire insertion guide with the longitudinal central canal of said metatarsal bone.

12. A method for pinning at least two elongated bones or bone portions together, as set forth in claim 11, wherein said moving said K-wire through said second bone until said wire is at a selected position in said second bone includes moving said K-wire through the longitudinal central canal of the metatarsal bone until it reaches the most proximal cortical end of the metatarsal bone whereat it is firmly fixated within cortical bone.

13. A method of pinning at least two elongated bones or bone portions together, as set forth in claim 6, wherein said wire insertion guide has said first end adapted to receive an end of said K-wire and guide said K-wire to said centrally disposed bore in said wire insertion guide, and said second end having said cavity defined therein adapted to receive the first end of said second bone.

14. A method of pinning at least two elongated bones or bone portions together, as set forth in claim 6, wherein said positioning a wire insertion guide between the first end of the first bone and the first end of the second bone includes:

moving said semicylindrical bodies to said closed position, inserting said wire insertion guide into a wound area between the first end of the first bone and the first end of the second bone, and aligning the second end of the wire insertion guide with the first end of said second bone, the first end of the wire insertion guide with the first end of said first bone, and coaxially aligning the central bore of the wire insertion guide with a central longitudinal canal of said second bone.

15. A method of pinning at least two elongated bones or bone portions together, as set forth in claim 6, wherein said method includes, subsequent to moving said K-wire through said second bone until said wire is at a selected position in said second bone, opening the wire insertion guide and removing said guide from said wound area.

* * * * *